United States Patent [19]

Huggins

[11] 4,045,525
[45] Aug. 30, 1977

[54] GAS HUMIDIFICATION APPARATUS

[76] Inventor: James A. Huggins, 551 W. Park Ave., Libertyville, Ill. 60048

[21] Appl. No.: 708,115

[22] Filed: July 23, 1976

Related U.S. Application Data

[63] Continuation of Ser. No. 480,843, June 19, 1974, abandoned.

[51] Int. Cl.² .......................... B01F 3/04; A61M 15/00
[52] U.S. Cl. .................................. 261/124; 128/186; 128/194; 222/400.7; 261/DIG. 65
[58] Field of Search ................. 261/78 A, 121 R, 122, 261/124, 123, DIG. 65; 222/3, 400.7; 137/525; 128/185, 186, 188, 194

[56] References Cited

U.S. PATENT DOCUMENTS

| 2,342,602 | 2/1944 | Reitz, Jr. | 261/124 X |
| 2,770,319 | 11/1956 | Hagenbook | 261/124 X |
| 3,572,660 | 3/1971 | Mahon et al. | 261/DIG. 65 |
| 3,682,168 | 8/1972 | Deaton | 261/122 X |
| 3,744,771 | 7/1973 | Deaton | 261/DIG. 65 |
| 3,771,721 | 11/1973 | Amerongen | 261/DIG. 65 |
| 3,806,102 | 4/1974 | Valenta et al. | 261/DIG. 65 |
| 3,834,385 | 9/1974 | Pekkarinen | 261/DIG. 65 |
| 3,834,682 | 9/1974 | McPhee | 261/DIG. 65 |

Primary Examiner—Tim R. Miles
Assistant Examiner—Richard L. Chiesa
Attorney, Agent, or Firm—Olson, Trexler, Wolters, Bushnell & Fosse, Ltd.

[57] ABSTRACT

Apparatus for administering humidified gas (e.g., oxygen) to a patient includes a plastic connector for connection to an oxygen supply and having an oxygen supply tube therein. A spike portion on the connector or on a diffuser at the lower end of the supply tube is caused to pierce the stopper in an intravenous solution bottle after which the supply tube is pushed to the bottom of the solution bottle. Oxygen from the supply tube is delivered to the bottom of the bottle through small holes at the bottom end of the supply tube or in the diffuser. The humidified oxygen enters a chamber formed by a part of the interior of the connector portion that is not occupied by the supply tube. The humidified gas then leaves the chamber and enters a conduit on the connector that is telescoped with a nasal cannula. The connector has a hole covered by the cannula tubing or by another piece of tubing such that the tubing expands upon excess pressure being in the connector to act as a safety valve.

13 Claims, 14 Drawing Figures

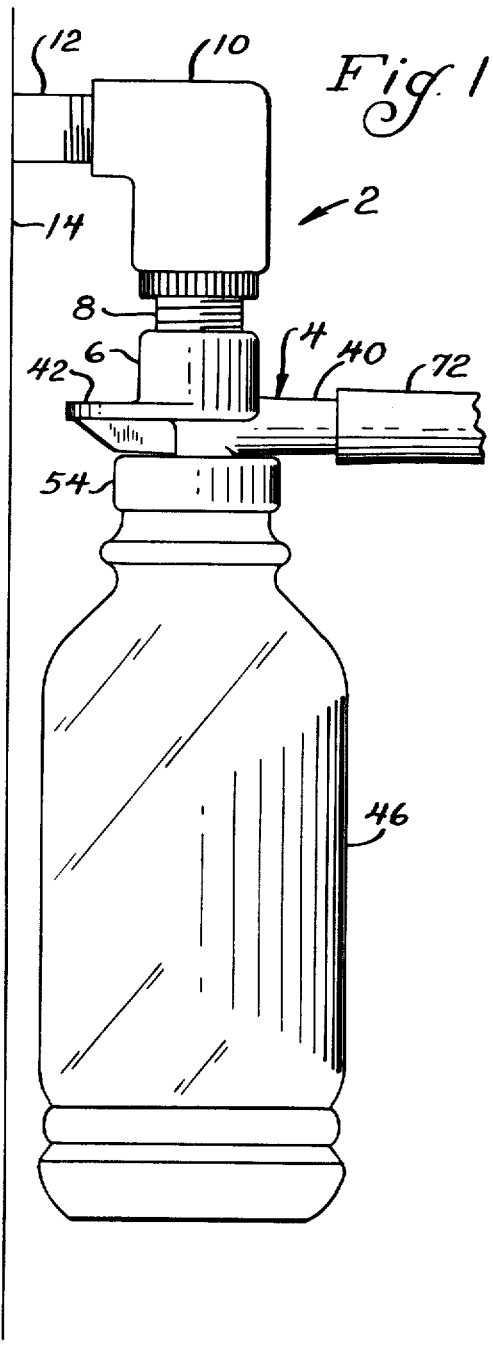
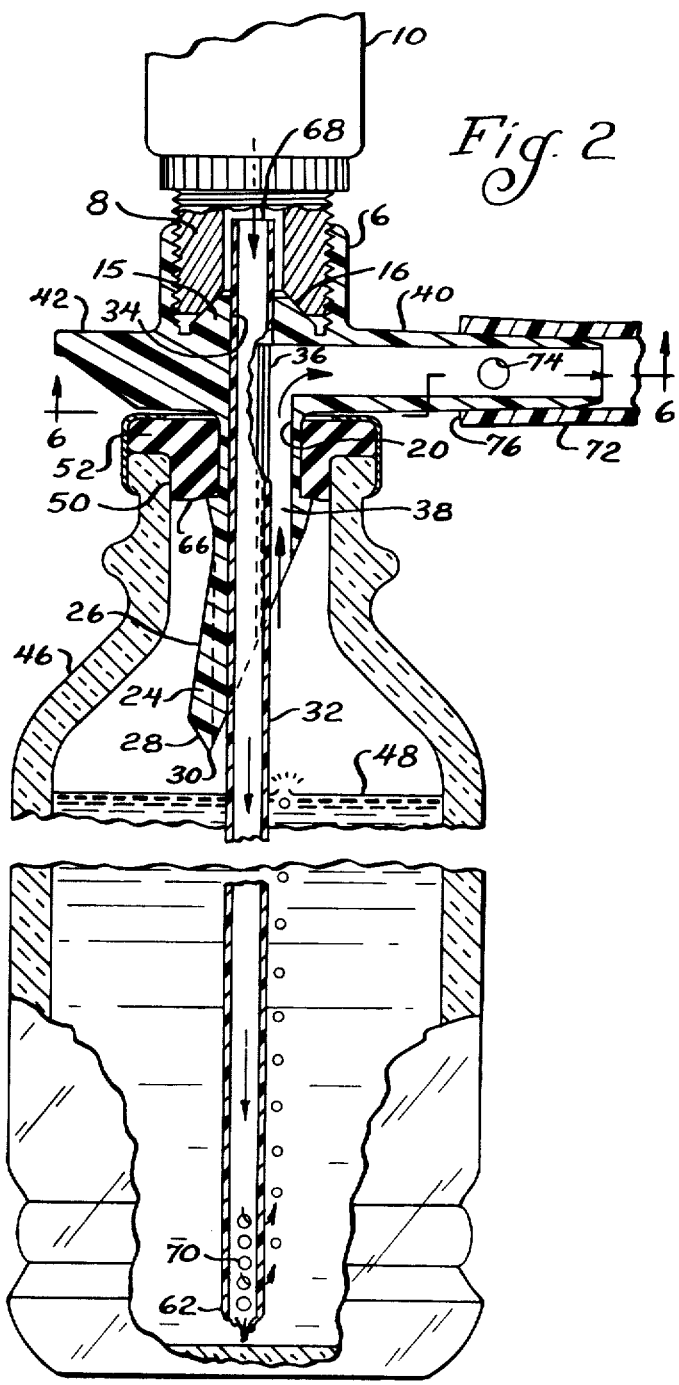

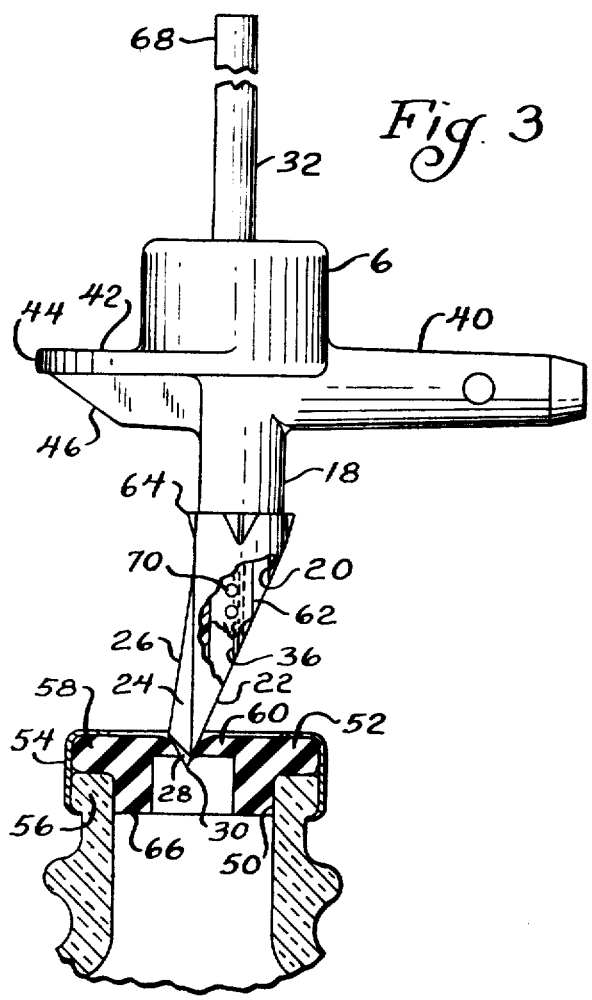
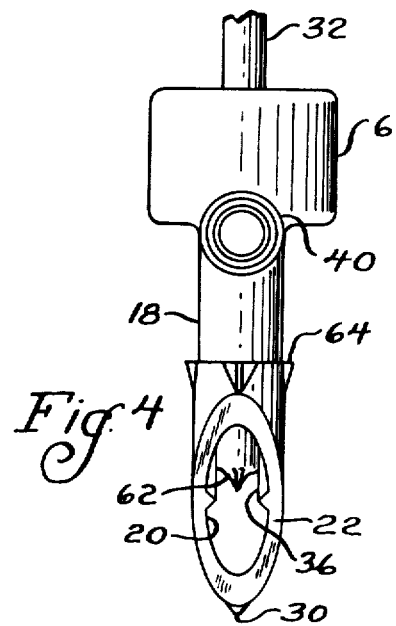
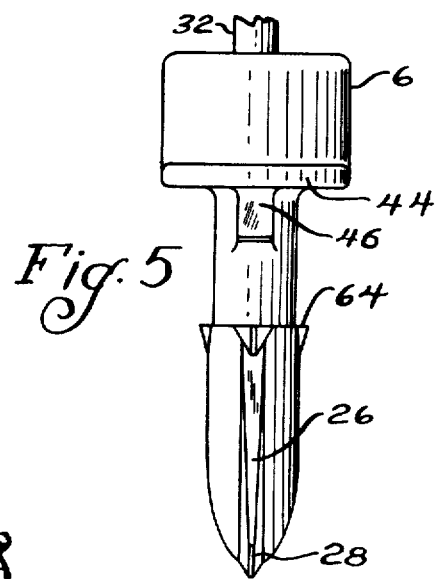
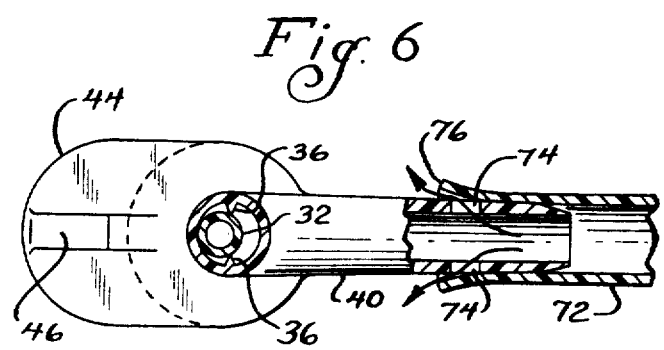

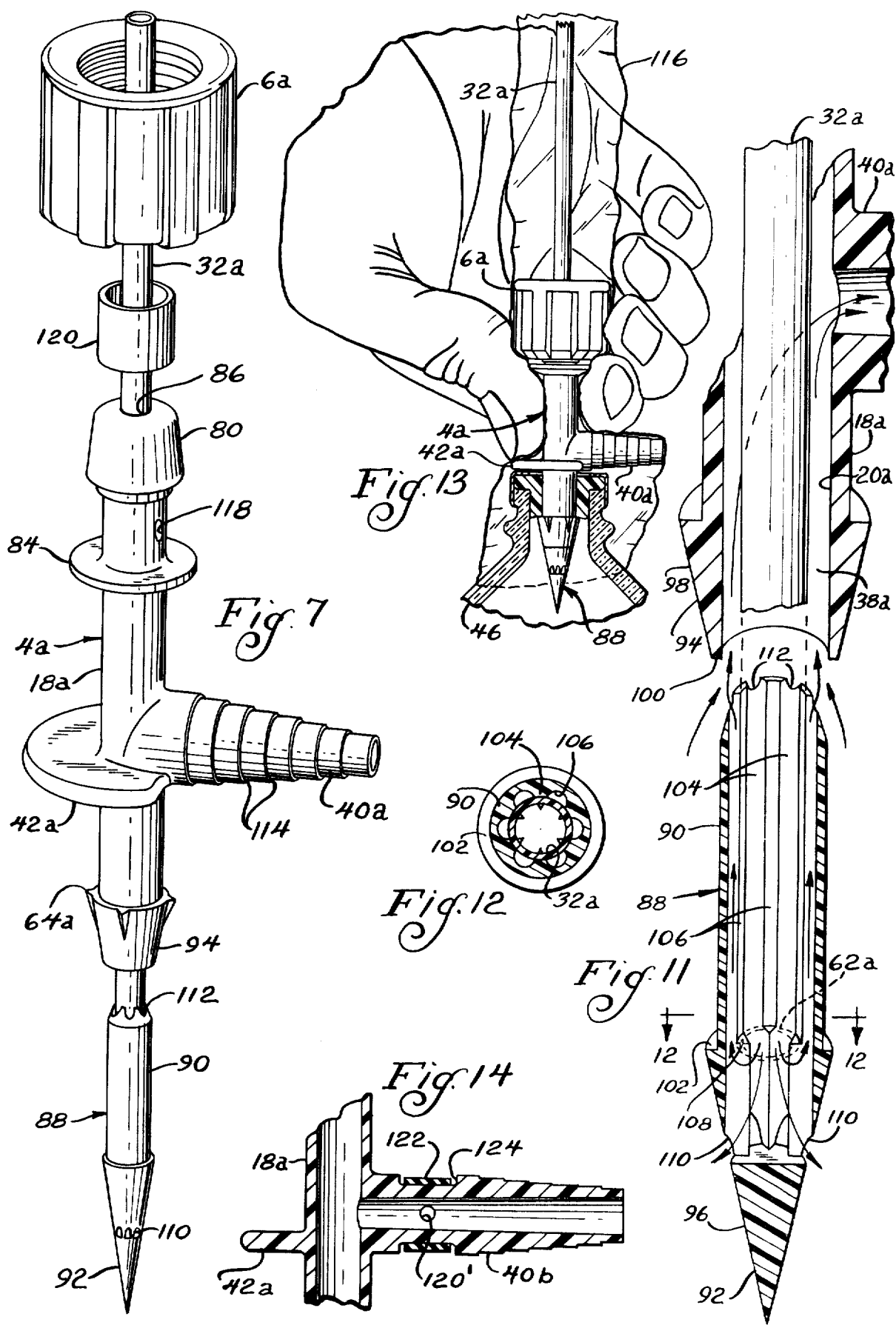

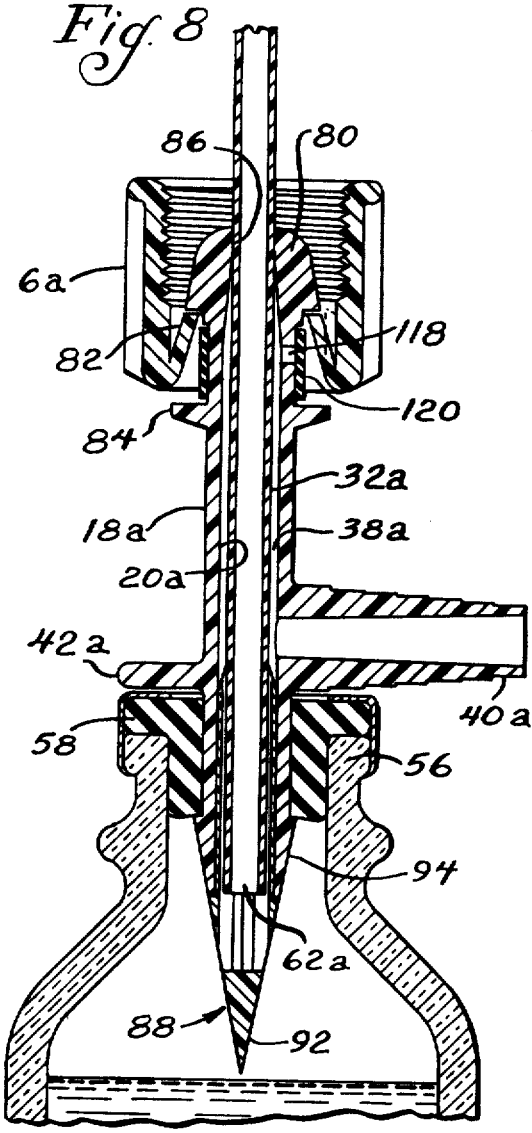
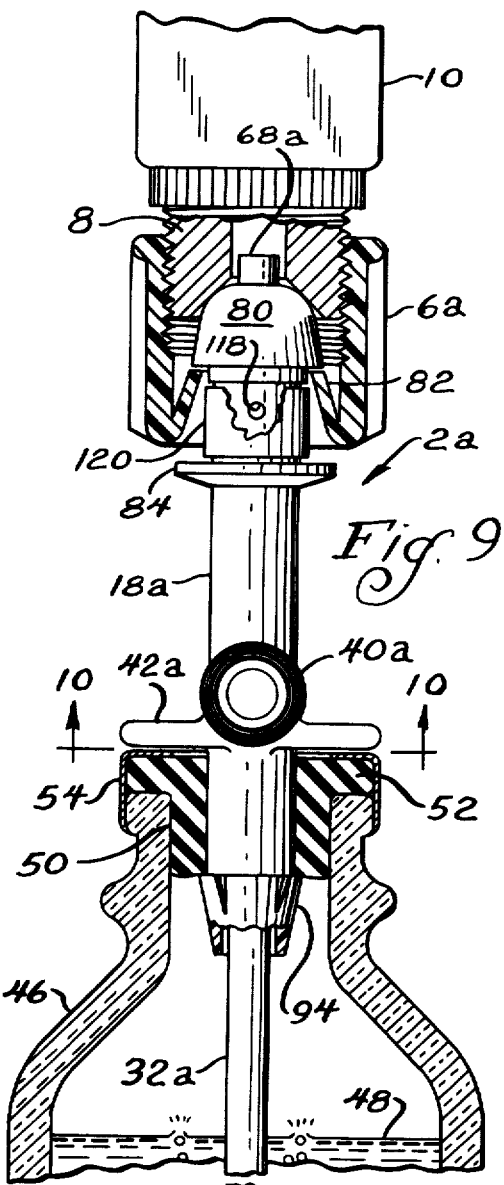
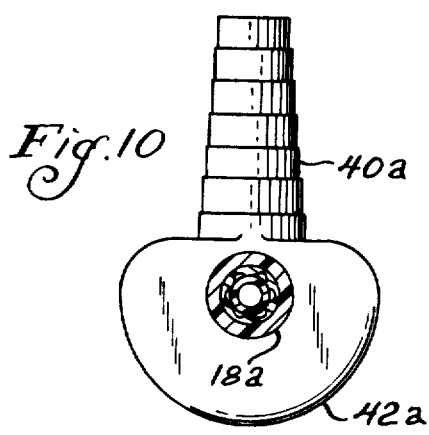
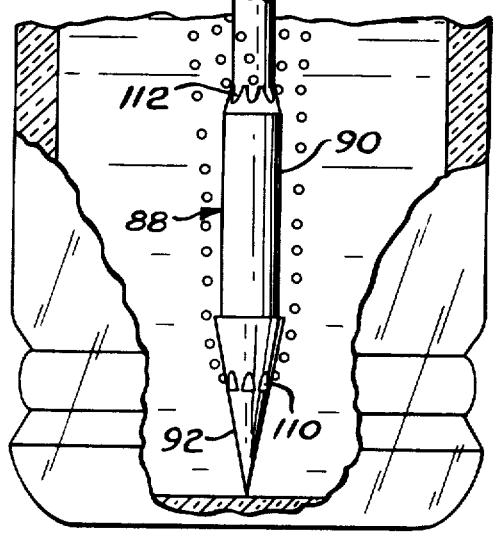

GAS HUMIDIFICATION APPARATUS

CROSS-REFERENCE TO RELATED APPLICATION

This application is a continuation of U.S. patent application Ser. No. 480,843, filed June 19, 1974, now abandoned.

Reference may be had to my copending application Ser. No. 312,670, filed Dec. 6, 1972, now U.S. Pat. No. 3,852,385.

BACKGROUND OF THE INVENTION

This invention relates to improvements in apparatus for gas humidification systems, particularly systems for humidifying oxygen prior to delivery to a patient. It is well known that the oxygen in conventional supply tanks used by hospitals has a relatively low humidity, and for this reason the oxygen cannot, in many instances, be directly administered to the patient. As a result, the oxygen is frequently passed through humidifiers prior to being delivered through a nasal cannula to the patient. The oxygen or oxygen-containing gas is usually humidified by bubbling the gas through a reservoir of water, saline solution, or other medicated solution.

In order to maintain sterility, it has been previously proposed to utilize a standard intravenous solution bottle as the reservoir through which the gas is bubbled. The intravenous solution bottle has the advantage that it contains its own sterilized supply of water or other solution. Also the bottle is disposed of after use. Thus, assuming proper handling procedures, sterility is preserved. However, in order for standard intravenous solution bottles to be used for this purpose it is desired, from the point of view of economy, that standard or nearly standard stoppers be used on the bottles.

When a standard stopper is used, it is necessary to puncture it and also to provide an arrangement that connects the oxygen supply to the apparatus. There must also be provided a supply of oxygen to the bottom of the bottle and also a means for delivery of the humidified gas to a nasal cannula. The set up or installation of the apparatus should be simple and yet maintain sterility. In particular there should be a minimum of difficulty in puncturing the stopper.

In operation of the apparatus it sometimes happens that the free flow of humidified gas is obstructed by an occlusion in the nasal cannula, which usually is a flexible tube. When this occurs, the pressure in the bottle and in the fittings of the system can become excessive.

OBJECTS AND SUMMARY OF THE INVENTION

An object of this invention is to provide a gas humidification system that is capable of utilizing conventional intravenous solution bottles having conventional stoppers therein, whereby the hospital does not need to inventory bottles with specially constructed stoppers solely for use with oxygen humidification apparatus and procedures.

A further object of this invention is to provide a novel connector which forms part of the system and which serves as the principal component that facilitates the use of conventionally stoppered intravenous solution bottles in the system.

It is a further and more specific object of the present invention to provide a connector of the type and for the purpose stated that is adapted to puncture a conventional or nearly conventional intravenous solution bottle stopper, and wherein the connector prevents accidental removal thereof from the bottle stopper while also permitting the bottle to be suspended from the connector.

It is another object of this invention to provide a connector of the type stated in which the lower end thereof has a spike portion that is relatively rigid and sharp so as to facilitate puncturing of the bottle stopper.

Another object of this invention is to provide a connector of the type stated that has a gas supply tube therein with a lower or outlet end initially adjacent to or recessed within the connector, the gas supply tube being capable of being axially shifted to position said outlet end at or near the bottom of the bottle after the stopper has been punctured and the connector is seated in place on the stopper.

A further object of this invention is to provide a connector of the type stated which is shaped to facilitate manipulation thereof for puncturing the stopper.

It is also an important object of this invention to provide a connector having a hole in a wall thereof that is covered by tubing to constitute a safety valve to relieve excess pressure in the connector.

A still further object of this invention is to provide an apparatus in which the lower or outlet end of the supply tube has a spike element constituting a part of the spike portion for penetrating the stopper and wherein such spike element is also a diffuser for the gas.

In accordance with the foregoing objects a connector of the present invention comprises a body with a first tubular means or coupling at one end for connection to a gas supply, such as the outlet of a metering valve. The gas is typically oxygen, but it may be ordinary air, or air modified by additional oxygen. The body also includes at its end opposite the coupling a second tubular means. A third tubular means in the connector body comprises a gas supply tube of smaller diameter than that of the second tubular means and telescoped therein. The second tubular means is sealed from the gas supply so that the gas flows through the gas supply tube, bypassing the second tubular means. The outlet end of the gas supply tube is initially proximate to an end of the second tubular means while the inlet end of the gas supply tube initially projects upwardly beyond the coupling. A spike portion for piercing the stopper of a container is provided either integrally with the second tubular means or in part on the second tubular means and in part on the lower end of the supply tube.

After the spike portion punctures and seats in the stopper, the inlet end of the gas supply tube is axially pushed so that its outlet end is at or near the bottom of the solution bottle. The outlet end of the gas tube is closed off except for a series of small holes through which the gas passes to the solution. Alternatively the spike element at the lower end of the supply tube provides a diffuser for discharging the gas. Barbs on the spike portion retain the connector in place and also permits the stoppered bottle to be suspended from the spike portion. Gas bubbling up from the outlet end of the gas supply tube diffuses through the solution and leaves the surface of the liquid in a humidified condition and then flows to a chamber that is formed by the surrounding part of the connector bore that is not occupied by the gas tube. This chamber is in communication with a conduit member constituting a fourth tubular means that is part of the connector body and which is adapted to be telescoped with nasal cannula for transmitting the humidified gas to the patient. A hole is provided in a wall of the connector and the hole is sealingly covered by flexible tubing. However, excess pressure in the connector will flex the tubing and gas will then escape via the hole, whereby the arrangement constitutes a safety valve.

BRIEF DESCRIPTION OF THE FIGURES

FIG. 1 is a side elevational view of a gas humidifying apparatus constructed in accordance with and embodying the present invention;

FIG. 2 is an enlargement of FIG. 1, partially broken away and in section;

FIG. 3 is a side elevational view, partially broken away and in section, of the connector of this invention and showing the same being inserted through the stopper of an intravenous solution bottle;

FIG. 4 is a front elevational view of the connector shown in FIG. 3;

FIG. 5 is a rear elevational view of the connector;

FIG. 6 is a fragmentary sectional view taken substantially along the line 6—6 of FIG. 2;

FIG. 7 is an exploded perspective view of parts of a modified form of apparatus;

FIG. 8 is a vertical section of the apparatus of FIG. 7 before the gas supply tube has been lowered to the bottom of the bottle;

FIG. 9 is a right hand elevational view of the apparatus of FIG. 8, partially in section, and showing the gas supply tube lowered, and also showing the connector coupled to a gas supply;

FIG. 10 is a fragmentary sectional view taken along line 10—10 of FIG. 9;

FIG. 11 is an enlarged fragmentary sectional view of a portion of the structure of FIG. 8, but partially exploded for clarity;

FIG. 12 is a sectional view taken along line 12—12 of FIG. 11;

FIG. 13 is a reduced scale elevational view, somewhat similar to FIG. 8 and partially in section, and showing the connector and supply tube on the bottle stopper after piercing of the stopper; and FIG. 14 is a fragmentary sectional view of a further modified form of connector.

DETAILED DESCRIPTION

Referring now in more detail to the drawing, and more particularly to FIGS. 1-6, there is shown a humidifying apparatus 2 that includes a connector 4 which is in the form of a one piece molded plastic body of high density polyethylene or other suitable material. The connector 4 includes at one end thereof a first tubular portion or coupling 6 for connection to a source of oxygen or other gas. More particularly, the coupling 6 is internally threaded for threaded connection to the tubular outlet fitting 8 that forms part of the discharge end of the gas supply valve 10. This valve 10 is used to control or meter the flow of gas into the humidification system. The control valve 10 may, as shown in FIG. 1, take the form of a right angle or elbow whereby the inlet end of the valve 10 is connected to a threaded nipple 12 that projects outwardly from a wall or other support 14. At the inner end of the coupling 6, the connector 4 has an internal boss 15 with a conical seat 16 that seals against the discharge end of the outlet fitting 8, as best shown in FIG. 2.

The connector 4 also integrally includes at another end thereof a second tubular portion in the form of a depending spike 18. The spike 18 has a bore 20 and a configuration at its lower portion that facilitates readily piercing the stopper of an intravenous solution bottle. More particularly, the spike 18 has a beveled portion 22 that extends downwardly to the tip of the spike. Opposite to the beveled portion 22 spike 18 is integrally formed with a chisel-like portion 24. This chisel-like portion 24 is in the form of a rib that extends downwardly with its outer surface 26 being at a small acute angle to the longitudinal axis of the spike 18. Near its lower end, the outer surface portion 26 angles abruptly inwardly and downwardly to provide a terminal portion 28. The portion 28 and the beveled portion 22 intersect to form an edge or point 30 at the tip of the spike for initial penetration of a bottle stopper.

Mounted within the connector 4 is a third tubular member or gas supply tube 32 which is preferably of the same material as that of the connector 4. The gas supply tube 32 is frictionally held within a bore 34 that is formed centrally of the boss 15. The gas supply tube 32 also projects upwardly into the bore of the outlet fitting 8, as shown in FIG. 2, so that gas being discharged at the fitting 8 will flow into the tube 32. The fit between the wall of the bore 34 and the outer surface of the gas supply tube 32 forms a seal sufficient to block the flow of the gas through the bore 34.

It will also be noted that the diameter of the bore 34 and the external diameter of the tube 32 are each substantially less than the diameter of the bore 20. Furthermore, it will be seen that the bores 34 and 20 are eccentric to one another such that the outer surface of the gas supply tube 32 is tangent to the wall of the bore 20 in the region thereof that is adjacent to the chisel portion 24. The connector 4 is also integrally molded with opposed longitudinal ribs 36, 36 in the bore 20 which serve to maintain the tube 32 tangent to the wall of the bore 20, as previously described. Preferably these ribs 36, 36 extend from the beveled portion 22 substantially up to the lower end of the boss 15. Since the gas supply tube 32 has an external diameter that is substantially smaller than the diameter of the bore 20, the bore 20 and the tube 32 cooperate to provide a chamber 38. Viewed another way, the chamber 38 is comprised of the part of the bore 20 that is not occupied by the gas supply tube 32.

Intermediate the coupling 6 and spike 18 the connector 4 integrally includes a fourth tubular means constituting a discharge conduit 40, and a hilt section 42. The conduit 40 runs generally perpendicular to the spike 18. The hilt section 42 includes a flange 44 and a radial rib 46. For reasons more fully appearing hereafter, the hilt section 42 and the conduit 40 cooperate to form a handle running transversely of the spike 18 for manipulating the connector 4 during piercing of a bottle stopper.

The intravenous solution bottle 46 is typically a glass container that constitutes a reservoir for liquid 48, which may be sterile water, saline solution, or other medicated solution. At the upper end of the bottle 46 there is an opening at which there is a closure, such as a rubber or rubber-like resilient stopper 52. The stopper is clamped in place by a metal clamping ring 54 that underlies the top bead 56 of the bottle and overlies the peripheral flange 58 of the stopper. The stopper 52 may also include a central section 60 which is adapted to be pierced when access to the contents of the bottle is desired. This section 60 may be relatively thin as shown in FIG. 3, or it might also be the full thickness of the stopper. In some instances the exposed part of the stopper may be covered with a disc to preserve sterility. If this is not done, the top of the stopper at the central section 60 may be wiped with an alcohol swab just prior to piercing the same.

The connector 4 and assembled gas supply tube 32 may be packed in a sterile package of flexible sheet material and with the lower or discharge end of the gas supply tube 32 recessed within the spike 18. Except for the sterile packaging (not shown) this initial condition of the connector 4 and gas supply tube 32 therein is shown in FIG. 3. The sterile packaging may be punctured (e.g., by the spike) or torn away in the region of the spike 18. The connector 4 may be grasped through the sterile packaging by gripping the handle that is formed by the hilt section 42 and the conduit 40. Thereafter, the spike may be pushed through the central section 60 of the stopper until the circumferentially disposed barbs 64 on the spike pass the lower margin or surface 66 of the stopper. These barbs 64 inhibit retraction of the spike 18 subsequent to mounting of the spike onto the stopper 52. Initially, and as shown in FIG. 3, the upper or inlet end of the gas supply tube projects axially outwardly beyond the coupling 6. However, after installation of the connector 4 on the stopper 52, the gas supply tube 32 is pushed outwardly of the end of the spike until its lower or discharge end 62 is at or near the bottom of the bottle 46, as shown in FIG. 2. The necessary manual force against the gas tube 32 may be applied through the sterile packaging. When a bottle of standard size is used, the length of the gas supply tube 32 will be made such that the inlet end 68 will be at or slightly below the upper edge of the coupling 6 when the discharge 62 is at the bottom of the bottle. Obviously, the length of the gas supply tube can be designed in accordance with the height of the particular bottle with which it is intended to be used.

The coupling 6 is then threaded on to the outlet fitting 8 until the latter seats against the conical seat 16. This may be easily done by manipulating the bottle 46. Firm tightening of the coupling 6 against the fitting 8 may, if needed, be effected by grasping and turning the hilt section 42 and/or coupling 6. At this time the bottle is suspended from the connector 4, as best shown in FIGS. 1 and 2.

It will be seen that the discharge end 62 of the gas supply tube 32 is pinched off, and this may be done by heating the gas supply tube thereat and pressing the tube closed during manufacture thereof. Furthermore, above the pinched off or closed extremity, the discharge end 62 is formed with a number of small holes 70 so that with the gas valve 10 opened, small bubbles of gas will pass from the tube 32 into the liquid 48 and rise from the surface thereof into the chamber 38 and from there pass into the conduit 40.

The conduit 40 has a slight external taper toward its discharge end and is adapted to telescope into a nasal cannula tube 72. This flexible nasal cannula tube 72 is of known construction and conveys the humidified gas to the patient. However, it sometimes happens that the nasal cannula tube may be occluded as, for instance, by being inadvertently constricted by the patient. When this occurs a pressure buildup takes place within the system, including the conduit 40. Accordingly, the present invention contemplates the provision of one or more holes 74, 74 in the wall of the conduit 40, which holes are normally adapted to be covered by the nasal cannula 72 in sealing relationship. However, when the pressure within conduit 40 and/or cannula becomes excessive, the part of the cannula at the holes 74 tends to flex or expand, as shown in FIG. 6, causing one or more of the holes 74, 74 to be uncovered and thereby relieve the excess pressure in the system. In telescoping the conduit 40 with the cannula tube 72, the cannula end 76 should be positioned just far enough past the holes 74, 74 so that the latter are sealingly covered in normal operation but leave a small amount of cannula material overlapping the holes for expansion and pressure release when the pressure in the conduit 40 reaches an ascertainable maximum.

A modified form of apparatus 2a is shown in FIGS. 8–13 in which like reference numerals indicate like parts that appear in arrangement of FIGS. 1–6. Furthermore, certain of the parts in FIGS. 8–13 that correspond to or are similar to parts in the apparatus of FIGS. 1–6 are indicated by a like reference numeral with the suffix a.

The plastic connector 4a has a coupling 6a at one end thereof constituting a first tubular portion for connection to the outlet fitting 8 of the gas supply. The coupling 6a is externally knurled or ribbed to facilitate manipulation thereof during threading of the coupling 6a onto the outlet fitting 8. The upper end of the connector body has a somewhat frusto-conical bulb 80 which cooperates with an upwardly and inwardly disposed conical skirt 82 in the coupling 6a. The skirt 82 is flexible so that it flexes radially outwardly to snap past the base or largest diameter portion of the bulb 80 when the coupling 6a is axially pushed over the bulb 80. An annular flange 84 on the connector body loosely confines the coupling 6a to the region of the bulb 80. Accordingly, the coupling 6a has a swivel fit on the connector body.

It will be apparent that when the coupling 6a is rotated relative to the connector body the bulb 80 is pressed into firm engagement with the conical seat 16 so as to form a seal. The gas from the supply source can flow directly to the gas supply tube of the connector for the same purposes as previously described.

The connector 4a also includes a second tubular portion 18a having a bore 20a which functions in a manner similar to the bore 20, previously described. The tubular portion 18a differs in certain respects from the spike portion 18a in that the tubular portion 18a has only a part of the spike whereas the gas supply tube carries another part of the spike, namely a spike element which does the actual piercing of the bottle stopper 52.

Mounted within the bore 20a is a third tubular means or gas supply tube 32a. Like the gas supply tube 32, the gas supply tube 32a has a smaller external diameter than that of the bore 20a. However, in this form of the invention the gas supply tube 32a concentric with the bore 20a, whereby the chamber 38a for receiving the humidified gas that bubbles up from the liquid is formed by the part of the bore 20a that surrounds the tube 32a. Furthermore, the tube 32a is frictionally held by a tapered bore portion 86 in the bulb 80, the tapered bore portion 86 being a tapered upper end of the bore 20a. The frictional fit between the tube 32a and the bulb 80 is sufficient to prevent the flow of gas through the bore portion 86. Nevertheless, the tube 32a can be shifted axially within the bore 20a with only a modest amount of force in order to lower the outlet end of the gas supply tube to the bottom of the bottle during installation of the connector assembly onto the bottle.

The outlet or discharge end 62a of the tube 32a telescopes within a plastic diffuser 88. This diffuser 88 comprises a tubular shank 90 of smaller diameter than the bore 20a so as to telescope therein when the gas tube is assembled and packaged with the remainder of the connector assembly. The diffuser 88 also includes a sharply pointed conical spike element 92 which serves to pierce the bottle stopper 52. It will also be noted that the lower end of the tubular portion 18a has a frusto-conical and barbed extension 94 that serves to inhibit retraction of the connector once assembled with the bottle stopper. Thus, when the gas supply tube 32a is in its "up" position (shown in FIGS. 8 and 13), the spike element 92 and the extension 94 abut one another at shoulders 100, 102 whereby the spike element 92 and extension 94 cooperate to form the spike portion of the connector assembly. Furthermore, when the shoulders 100, 102 abut one another the conical surface 98 of the extension 94 forms a smooth and continuous extension of the conical surface 96 whereby puncturing of the stopper 52 is readily facilitated.

Referring again to the diffuser 88, it will be seen that the bore of the shank 90 is formed with circumferentially disposed divider elements or splines 104 that cooperate with the part of the tube 32a that is telescoped within the shank 90 to form a series of longitudinal passageways 106. The outlet end 62a of the supply tube 32a seats against an abutment or shoulder 108 at the lower end of the shank 90. However, as best seen in FIG. 11, the passageways 106 extend downwardly beyond the shoulder 108 and into the conical spike element 92, whereby the passageways 106 terminate in a group of circumferentially spaced lower gas discharge openings 110. The upper ends of the passageways 106 terminate in a second group of circumferentially spaced discharge openings at the upper end of the shank 90.

The diffuser 88 may be molded utilizing a core with, for example, six splines to form the passageways 106. Thus, by having the splines on this core piece extend beyond the shoulder 108 and to the conical surface of the spike element 92, it is possible to form 12 openings for gas discharge and yet use a core piece with only six splines, thereby reducing tooling costs. Furthermore, by having the groups of gas discharge openings 110, 112 spaced longitudinally of the diffuser, there is provided a series of gas discharge openings that result in an improved diffusion of gas through the liquid.

The diffuser 88 is molded as a separate piece. Thereafter, tubing of the proper length and constituting the tube 32a is inserted within the shank 90 until outlet end 62a of the tube 32a engages the shoulder 108. The diffuser 88 and the gas tube 32a may have a friction fit, as by tapering the shank 90, or the tube 32 and the shank 90 may be solvent or otherwise bonded together.

The connector 4a also includes a hilt section 42a which is generally perpendicular to the longitudinal axis of the bore 20a. This hilt section 42a is somewhat thinner than the hilt section 42, previously described, although it serves essentially the same purpose.

Also integrally included on the connector 4a is a fourth tubular means constituting a conduit 40a for conveying the humidified gas from the chamber 38a. As best seen in FIG. 7, the conduit 40a may have a series of steps or ridges 114 for receiving flexible cannula tubing of the type shown at 72 in FIGS. 2 and 6. The conduit 40a is, like the conduit 40 previously described, substantially at right angles to the axis of the bore 20a, whereby the hilt section 42a and the conduit 40a constitute a handle to facilitate manipulating the connector assembly when piercing the bottle stopper, as best shown in FIG. 13.

With continued reference to FIG. 13, it will be seen that the connector assembly may be packaged in a sterile transparent wrapper 116 and can be manually manipulated through the wrapper by grasping the tubular section 18a and by engaging the hilt 42a with the thumb and the conduit 40a with the forefinger. Initially, the upper or inlet end 68a of the tube 32a is substantially above the coupling 6a and the spike element 92 is in abutting relation with the extension 94. With the end of the wrapper 116 opened and preferably covering the top portion of the bottle, the spike made up of the spike element 92 and extension 94 is forced through the bottle stopper 52 until the extension 94 with the barbs 64a thereon reach the lower margin or surface 66 of the stopper. The gas supply tube may then be gripped through the sterile wrapper 116 and pushed downwardly until the upper or inlet end 68a of the gas tube is just above the bulb 80. The length of the tube 32a is made such that for standard intravenous solution bottles, the inlet end 68a will be approximately in the position shown in FIG. 9 when the tip of the spike element 92 engages the bottom of the bottle. The sterile wrapper may then be removed and the coupling 6a threaded onto the outlet fitting 80 until the bulb 80 seals against the conical surface 16. Thereafter, the nasal cannula tubing may be telescoped over the conduit 40a.

When gas is supplied to the tube 32a, the gas will flow from the discharge end 62a downwardly to the lower openings 110 through passageway portions in the spike element 96. The gas will also flow upwardly around the tube 32a through the passageways 106 to the upper openings 112. The humidified gas then flows into the chamber 38a and from there into the bore of the conduit 40a for delivery to the nasal cannula, as shown by the flow-indicating arrows in FIG. 11.

In the apparatus of FIGS. 8–13, the part of the tubular portion 18a that is between the flange 84 and the bulb 80 has a hole 118 that is covered by a piece of resilient tubing 120. The hole 118 is exposed to the humidified gas pressure so than when the humidified gas reaches an ascertainable maximum, the tubing will flex and uncover the hole to relieve the excess pressure. The tubing 120 will be designed, in terms of thickness and resiliency, for the desired pressure relief. Furthermore, the tubing 120 is easily assembled with the tubular portion 18a by simply stretching tubing 120 over the bulb 80 and moving the tubing therepast until the tubing snaps around the tubular portion 18a that is just above the flange 84.

In the further modified form of the invention shown in FIG. 14 the connector and other parts of the apparatus are similar to that in FIGS. 8–13 except for the location of pressure relief valve. In FIG. 14 there is a hole 120' in wall of a conduit 40b, the latter being modified as compared to conduit 40a. The conduit 40b has a peripheral recess 124 at which the hole 120' is located, and the tubing 122 may be stretched and axially moved over the conduit 40b until it seats at the recess 124.

The advantage of using a separate piece of resilient tubing for the safety valve as compared to using the resilient tubing of the cannula lies in the fact that the pressure at which the valve opens can be more easily preset or established at the factory. There are various sizes of cannula tubing and they may have various resilient characteristics, all of which may make it difficult to establish a proper opening pressure for the relief valve.

The device of FIGS. 8-14 can also be used with a bag or like container having a tubular neck with an inset sealed diaphragm. The spike element 92 first pierces the diaphragm and then the extension 94 enlarges the diaphragm opening and keeps the diaphragm from sealing around the gas supply tube. Such bags or containers are known in the art.

The invention is claimed as follows:

1. In a connector for a gas humidification apparatus that includes a container of the type having a sealed but pierceable closure, a body having a tubular portion and a gas supply tube axially slidable therein, said gas supply tube being of substantially smaller diameter than that of said tubular portion to form a chamber by the part of the bore of said tubular portion that is unoccupied by said gas supply tube, said gas supply tube having an outlet end with a diffuser thereon, cooperating means comprised of an exterior wall portion of the tube disposed about and spaced from an interior wall portion on said diffuser and including divider elements forming a series of individual passageways communicating with said chamber and running longitudinally of said diffuser and exteriorly of said tube, said passageways also communicating with said outlet end and terminating in groups of gas discharge openings spaced longitudinally along said diffuser, said individual passageways defining gas flow channels from the gas supply tube to the interior of said container, and means on said diffuser for piercing the pierceable closure.

2. A connector for use in a gas humidification apparatus that includes a container with liquid and an opening with a closure therein, said connector comprising a body, first tubular means on said body for connection to a gas supply, second tubular means on said body having an end portion shaped for inhibiting removal of the body from the container closure, third tubular means in said second tubular means and being in communication with said first tubular means, said third tubular means and said second tubular means defining a chamber that is part of the bore of said second tubular means, said third tubular means being a gas supply tube having an outlet end initially adjacent to said end portion of said second tubular means and being movable axially in said second tubular means to position said outlet end remote from said end portion of said second tubular means, thereby to supply gas below the liquid level, the humidified gas then flowing into said chamber, a diffuser at said outlet end, said diffuser having a piercing point for penetrating said closure and a series of spaced openings through which the gas is adapted to pass, and in which said diffuser has a splined bore, said gas supply tube outlet end is in said bore, and the splines of said bore cooperate with said gas supply tube to provide longitudinal passages in said diffuser, adjacent ends of said passages terminating in at least some of said series of openings, and fourth tubular means forming a conduit for conveying humidified gas from said chamber.

3. A connector according to claim 2 in which said bore terminates in a shoulder for abutment by said outlet end, and said splines extend beyond said bore in communication with said outlet end and terminate at a surface of said diffuser in the provision additional of said series of openings.

4. A connector according to claim 2 in which one of said second and fourth tubular means has a hole in the wall thereof, and a resilient tube surrounds said wall and covers said hole to constitute a safety valve that uncovers the hole when the humidified gas pressure reaches as ascertainable maximum.

5. A connector for use in a gas humidification apparatus that includes a container with liquid and an opening with a closure therein, and wherein the closure is of a type having sealed but rubber or rubber-like resilient pierceable structure of standard thickness; said connector comprising a body, first tubular means on said body for receiving gas from a gas supply and comprising a threaded coupling cooperable with said body for connection to a gas supply, second tubular means on said body having an end portion, third tubular means in said second tubular means, said third tubular means and said second tubular means defining a chamber that is part of the bore of said second tubular means, one of said second and third tubular means having a sharp penetrating end for piercing the pierceable structure of said container closure, said end portion having means shaped for enlarging the pierced hole and means engaging said pierceable structure for inhibiting withdrawal of said body from said closure, said third tubular means having an outlet end initially proximate to said end portion of said second tubular means, said third tubular means being axially slidable in said second tubular means to position said outlet end remote from said end portion of said second tubular means for disposition of said outlet and substantially below the liquid level of the container, means for forming a seal between said gas supply and said second tubular means to provide a gas flow path to said third tubular means and into the liquid bypassing said second tubular means, the gas being humidified by the liquid and the humidified gas then flowing from the surface of the liquid into said chamber, and means on said body and constituting a fourth tubular means that is a conduit externally shaped for receiving flexible cannula tubing for conveying said humidified gas from said chamber to a patient.

6. A connector according to claim 1 in which one of said second and fourth tubular means has a hole in a wall thereof, and an annular piece of resilient tubing covering said hole to provide a safety valve that flexes to uncover said hole when the pressure of the humidified gas at said hole reaches an ascertainable maximum.

7. A connector according to claim 1 in which said conduit is generally perpendicular to said second tubular means, said body also having a hilt section that cooperates with said conduit to form a handle running generally transversely of said second tubular means for manipulating the connector during piercing of the closure, said hilt section including a relatively planar flange adjacent to said conduit.

8. A connector according to claim 1 in which said piercing structure is a spike element on the outlet end of said third tubular means.

9. A connector according to claim 8 in which said spike element is a diffuser for said gas.

10. A connector according to claim 1 in which said piercing structure and said structure for inhibiting withdrawal of said body from said closure are integral.

11. A connector according to claim 1 including a hilt section running generally transversely of said second tubular means for manipulating the connector during piercing of the closure.

12. Apparatus for administering humidified gas, such as humidified oxygen, to a patient comprising a container with liquid and having an opening with a closure thereacross, a connector assembly including means for connection to a gas supply and a tubular member, said connector assembly also including a gas supply tube in the bore of said tubular member and being in communication with said gas connection means, piercing means carried by said connector assembly for penetrating said closure and projecting therethrough, said gas supply tube extending beyond said end of the tubular member and being immersed in said liquid to supply gas thereto, means forming a chamber that is part of said bore for receiving humidified gas rising from the surface of said liquid, a conduit forming part of said connector assembly for conveying the humidified gas from said chamber, and a nasal cannula tube connected to said conduit, said connector assembly having a diffuser on said gas supply tube immersed in said liquid, said diffuser having a series of longitudinal splines that cooperate with the gas supply tube to form passageways that provide spaced groups of gas discharge openings.

13. Apparatus according to claim 12 in which said piercing means includes a piercing element on said gas supply tube and another element on said tubular member, said last mentioned element including means for inhibiting separation of the connector from the closure.

* * * * *